| United States Patent [19] | [11] | 4,393,203 |
|---|---|---|
| Mao et al. | [45] | Jul. 12, 1983 |

[54] PROCESS OF PREPARING ALKYLPOLYSACCHARIDES

[75] Inventors: Mark H. K. Mao, Cincinnati; Larry E. Miller, Madeira; John M. Weeman, Cincinnati, all of Ohio

[73] Assignee: The Procter & Gamble Company, Cincinnati, Ohio

[21] Appl. No.: 371,693

[22] Filed: Apr. 26, 1982

[51] Int. Cl.³ .......................... C07G 3/00; C07H 1/00; C08B 37/00
[52] U.S. Cl. ..................... 536/124; 159/49; 159/DIG. 10; 536/4.1; 536/18.4; 536/120
[58] Field of Search .................. 159/DIG. 10, 49; 536/4.1, 120, 124, 127

[56] References Cited

U.S. PATENT DOCUMENTS

| 2,049,758 | 8/1936 | Bertsch et al. | 536/4.1 |
|---|---|---|---|
| 2,390,507 | 12/1945 | Cantor | 536/4.1 |
| 2,671,780 | 3/1954 | Gaver et al. | 536/111 |
| 2,671,781 | 3/1954 | Gaver et al. | 536/111 |
| 2,959,500 | 11/1960 | Schlapfer et al. | 127/37 |
| 2,974,134 | 3/1961 | Pollitzer | 536/120 |
| 3,092,618 | 6/1963 | Rosen et al. | 536/103 |
| 3,219,656 | 11/1965 | Boettner | 536/18.3 |
| 3,314,936 | 4/1967 | Ames | 536/120 |
| 3,346,558 | 10/1967 | Roth | 536/18.6 |
| 3,450,690 | 6/1969 | Gibbons et al. | 536/18.5 |
| 3,547,828 | 12/1970 | Mansfield et al. | 252/351 |
| 3,598,865 | 8/1971 | Lew | 536/4.1 |
| 3,640,998 | 2/1972 | Mansfield et al. | 536/18.3 |
| 3,707,535 | 12/1972 | Lew | 536/18.6 |
| 3,721,633 | 3/1973 | Ranauto | 252/527 |
| 3,737,426 | 6/1973 | Throckmorton et al. | 536/18.3 |
| 3,777,269 | 11/1973 | Lew | 375/67 |
| 3,839,318 | 10/1974 | Mansfield | 536/18.6 |
| 4,011,389 | 3/1977 | Langdon | 536/4.1 |
| 4,154,706 | 5/1979 | Kenkare et al. | 252/547 |
| 4,187,121 | 2/1980 | Herald et al. | 134/26 |
| 4,223,129 | 9/1980 | Roth et al. | 536/18.6 |
| 4,240,921 | 12/1980 | Kaniecki | 252/156 |
| 4,309,447 | 1/1982 | Tsutsumi et al. | 424/361 |

FOREIGN PATENT DOCUMENTS 593422 2/1934 Fed. Rep. of Germany .
3001064 7/1981 Fed. Rep. of Germany .

OTHER PUBLICATIONS

The Journal of The American Chemical Society, vol. 60, (Sep. 1938), pp. 2076-2077, Noller et al.
Nature, vol. 197, (Mar. 16, 1963) Schram et al.
Several Data Sheets, Rohm & Haas Co., Material Safety Data Sheet, Coded 6-1843; a page entitled "Manufacturing Specifications", Triton BG-10; A Specialty Chemicals Price List, schedule CS-429,25; a publication entitled The Qualitative and Quantitative Determination of Triton BG-10 in Bottle Washing Formulations", Coded CS-400.
The Journal of The American Oil Chemist's Society, vol. 47, #5, (May 1980), pp. 162-167, Hughes et al, "Physical and Functional Properties of Some Higher Alkyl Polyglucosides".

Primary Examiner—Donald B. Moyer
Assistant Examiner—C. J. Faraci
Attorney, Agent, or Firm—Robert B. Aylor; Richard C. Witte; Thomas H. O'Flaherty

[57] ABSTRACT

Long chain fatty alcohols can be removed from alkylpolysaccharide products in thin film evaporators to achieve fatty alcohol levels of less than about 2% without excessive discoloration of the alkylpolysaccharide.

5 Claims, No Drawings

PROCESS OF PREPARING ALKYLPOLYSACCHARIDES

TECHNICAL FIELD AND BACKGROUND ART

This invention relates to an improved process for making alkylpolysaccharides in which the alkyl group contains from about 12 to about 18 carbon atoms and the polysaccharide chain contains from about 1½ to about 30 saccharide units. The improved process gives a good polysaccharide chain length distribution and a good color. The process can be used to prepare highly efficient alkylpolysaccharides useful as detergent surfactants and foam builders for anionic detergent surfactants.

SUMMARY OF THE INVENTION

The present invention relates to a process for preparing a long chain alkyl polysaccharide comprising the essential step of reacting a short chain alkylsaccharide of a reducing saccharide containing from about five to about six carbon atoms in which the alkyl contains from one to about five carbon atoms with a long chain fatty alcohol containing from about 12 to about 18 carbon atoms at a reaction temperature of from about 90° C. to about 120° C. in the presence of an acid catalyst, the resulting short chain alcohol being removed, preferably under a vacuum, and preferably as rapidly as possible, with the catalyst being destroyed by adding an alkaline material after at least about 90% of the short chain alkyl saccharide has been destroyed, the extent of destruction can be determined by measuring the resulting short chain alcohol which has been removed, and before the average polysaccharide chain length exceeds about 20, preferably before the length exceeds about 4, most preferably before the length exceeds about 3.

In a second highly preferred step the unreacted long chain fatty alcohol in the product from the above step is removed by applying a vacuum and heat to a thin film of the product of the first step whereby the unreacted fatty alcohol is reduced to a level of less than about 2%, preferably less than about ½%.

The combination of the above two steps can be used to provide a superior alkylpolysaccharide for use as a detergent surfactant in which the alkyl group contains from about 12 to about 18, preferably from about 12 to about 14 carbon atoms, the average polysaccharide chain length is from about 1½ to about 3, preferably from about 1.6 to about 2⅔ saccharide units, the level of short chain alkylsaccharide and polysaccharide is less than about 10%, the amount of alkylpolysaccharide in which the saccharide chain length is 6 or greater is less than about 10%, preferably less than about 5%, the alkylmonosaccharide content is less than about 60%, preferably less than about 50%, and the unreacted fatty alcohol content is less than about 2%, preferably less than about ½%.

DETAILED DESCRIPTION OF THE INVENTION

The fatty alcohols useful herein may be primary or secondary alcohols having straight or branched chains which can be either saturated or unsaturated, and may contain ether linkages. Preferably, the alcohols are primary saturated alcohols. Examples include dodecyl, tridecyl, tetradecyl, pentadecyl, hexadecyl, and octadecyl alcohols, and mixtures thereof. The preferred fatty alcohols are those containing from about 12 to about 14 carbon atoms.

The short chain alkylmonosaccharides, are e.g., the methyl, ethyl, propyl, butyl, and pentyl, preferably propyl or butyl, and most preferably butyl, fructosides, glucosides, mannosides, galactosides, talosides, allosides, altrosides, idosides, arabinosides, xylosides, lyxosides, ribosides, and mixtures thereof. The preferred alkylmonosaccharides are glucosides and fructosides due to their availability and low cost, and the most preferred alkylmonosaccharide is an alkyl glucoside. These compounds can be prepared separately, in a preliminary step, or as part of the first step since the corresponding short chain alcohols react with the corresponding reducing saccharides containing from five to six carbon atoms much faster than the long chain fatty alcohols react.

The molar ratio of the long chain fatty alcohol to the short chain alkylmonosaccharide is between about 1:4 and about 4:1, preferably between about 1:2 and about 2:1, most preferably between about 1:1 and about 1.2:1. The level of long chain fatty alcohol is preferably kept as low as possible to facilitate the removal of unreacted fatty alcohol from the desired alkyl polysaccharide. An auxiliary solvent can be used to maintain fluidity. The lower levels of fatty alcohol also maximize the formation of the desired long chain alkylpolysaccharides especially at levels above about 60%. Preferably the level of long chain alkylmonosaccharide in the finished product is less than about 60%, most preferably less than about 50%.

The reaction is carried out at a temperature of from about 90° C. to about 120° C., preferably above about 100° C. Above about 120° C. there is excessive formation of colored materials and excessively fast saccharide chain growth. However, the reaction temperature should be as high as possible to minimize the time of the reaction.

If an auxiliary solvent is used, it should have a boiling point that will permit its easy removal for recycling. It should also be compatible with the short chain alcohol, the long chain alcohol, the saccharide and the alkyl saccharides and should not be reactive. Suitable auxiliary solvents include: toluene, $C_{8-12}$ hydrocarbons, etc.

It is desirable that the resulting product contain a minimum of the short chain alkylsaccharides, which do not provide any detergency benefits. However, care must be taken in removing the last amount of the short chain alcohol since this normally requires more stringent conditions and one wants to avoid removal of the long chain alcohol. Furthermore, if the reaction proceeds for too long a time, the average polysaccharide chain length becomes too long. Increasing the reaction time can be used to achieve longer polysaccharide chains since free saccharide reacts with the end of the saccharide chain preferentially as compared to the fatty alcohol. Accordingly, it is desirable to remove the short chain fatty alcohol rapidly and kill the catalyst by adding an alkaline material as soon as the desired product is achieved. The combination of vacuum and temperature should not remove the long chain alcohol, however. Preferably the reaction takes place in a thin film, preferably at high Reynolds numbers, to permit rapid removal of the short chain alcohol which results and preferably the reaction takes place under a vacuum to assist in the rapid removal of the resulting short chain alcohol. Thin films can be achieved using, preferably, a wiped film evaporator or a drum evaporator, or mills in which two cylinders combine to form a thin film, etc. In a mill it is desirable that one of the cylinders rotate faster than the other to impart a shearing and mixing action. The reaction mix is conveniently removed from a drum or cylinder by a doctor blade.

The acid catalysts can be any of the conventional acids such as sulfuric acid, hydrochloric acid, phosphoric acid, phosphorus acid, toluene sulfonic acid, etc., and other Lewis acid catalysts, etc. The amount of acid catalyst used is between about 0.0001 mole per mole of saccharide monomer and about 0.02 mole per mole of saccharide monomer, preferably between about 0.005 and about 0.01, most preferably between about 0.001 and about 0.006. The amount of catalyst used can control the speed of reaction. When larger amounts of catalysts are used the neutralized catalyst should be one that is compatible with the end use of the surfactant. Sulfuric acid is the preferred catalyst.

REMOVAL OF THE FATTY ALCOHOL

The fatty alcohol can be removed from the product of the first step by distillation or by a solvent extraction technique. The fatty alcohol and any auxiliary solvent are removed after the catalyst has been destroyed by neutralization. The preferred method of fatty alcohol removal is to form a thin film of the reaction product containing the neutralized catalyst and apply heat and a vacuum. A wiped film evaporator is a particularly preferred piece of equipment for removing the fatty alcohol. Although the prior art represented by German OLS. No. 3,001,064 has described the problem associated with removing fatty alcohol from an alkyl polysaccharide without causing an increase in the color, it has now been found that the use of a thin film evaporator and a vacuum permits the removal of the fatty alcohols and/or solvent of this invention to a level below about 2% and even below about ½% without any appreciable change in the color of the product. This discovery is especially important when one is preparing alkylpolysaccharides from alcohols containing more than 10 carbon atoms where the boiling point of the fatty alcohol, even under a high vacuum, is very high and prolonged exposure to high temperature leads to decomposition of the polysaccharide.

In the removal process of this invention the product is formed into a thin film at a temperature of from about 120° C. to about 200° C., preferably from about 140° C. to about 180° C., most preferably from about 160° C. to about 170° C. is used and a vacuum of from about 0.1 mmHg to about 20 mmHg, preferably from about 0.1 mmHg to about 5 mmHg, most preferably from about 0.1 mmHg to about 3 mmHg is used. The thin film is preferably formed in a thin film evaporator which gives a film with a thickness of from about 1 mm to about 10 mm and a Reynolds number of at least about 20,000, preferably at least about 50,000, and more preferably about 100,000. The film in such evaporator is preferably less than about 5 mm in the wave and less than about 5 mm at its thinest.

PREFERRED PRODUCT

The process defined hereinbefore can be used to prepare a preferred alkylpolysaccharide detergent surfactant having superior properties with respect to detergency and suds boosting for other detergent surfactants. This preferred alkylpolysaccharide has the formula $RO(Z)_x$ is which R is an alkyl group containing from about 10 to about 18 carbon atoms; Z represents a 5 or 6 membered reducing saccharide moiety; x averages from about 1.5 to about 2.7; the amount of alkylpolysaccharide in which x is greater than 6 is less than about 10%, preferably less than about 5%; the amount of the alkylpolysaccharide in which x is 1 is less than about 60%, preferably less than about 50%, and the defined material is associated with no more than about 10% alkylsaccharides and polysaccharides wherein the alkyl group contains less than about 8 carbon atoms and with no more than about 2% alcohol containing an R group.

Preferably in the above compound R is a straight chain saturated alkyl group and preferably the R groups contain from about 12 to about 14 carbon atoms. An even more preferred average of x is from about 1.7 to about 2.5. The preferred Z group is a glucoside group.

The above preferred alkylpolysaccharide preferably constitutes at least about 90% of the alkylpolysaccharide material present. It is difficult to achieve an alkylpolysaccharide having the appropriate alkyl chain length and average x without either exceeding the desired amount of fatty alcohol or monosaccharide on the one hand, or providing excess material in which x exceeds 6 on the other hand. It is also difficult to maintain a good color in alkyl polysaccharide detergent surfactants to permit their incorporation into detergent compositions, and to minimize the amount of short chain alkylpolysaccharide present.

The process described hereinbefore achieves the desired product by minimizing the temperature to which the material is exposed, especially while an acid catalyst is present; maximizing the speed at which the short chain alcohol is removed; killing the catalyst as soon as the desired end point has been reached; and then removing the fatty alcohol, preferably by a process which minimizes the time and the temperature to which the desired product is exposed.

Surprisingly, it has been discovered that the increase in the alkyl chain length from 10 to 12 results in a very large decrease in the reactivity of the fatty alcohol. It also increases considerably the difficulty involved in removing the fatty alcohol without exceeding the decomposition temperature of the polysaccharide chain. The combination process disclosed herein achieves the desired product.

The importance of the limits on the preferred alkylpolysaccharide detergent surfactant are documented hereinafter in the examples. In order to obtain maximum performance, x needs to be as low as possible while maintaining water solubility. The desired products have an HLB of from about 7 to about 30, preferably from about 10 to about 20, and a critical micelle concentration of from about 10 ppm to about 1000 ppm, preferably from about 20 ppm to about 500 ppm.

EXAMPLE I 50 ml of n-butanol, 10 g anhydrous glucose, 20 ml n-dodecanol and 0.0534 g of p-toluene sulfonic acid were added to a 100 ml 3-neck flask with stirring. The reaction mixture was refluxed at 115°–117° C. for 2 hours. The n-butanol was then removed as fast as possible with the help of partial vacuum while keeping the temperature at 100° C. to 120° C. The reaction was kept at 120° C., 5 cm Hg vacuum for 40 minutes. 0.027 g of $Na_2CO_3$ was used to neutralize the reaction mixture. The unreacted n-dodecanol was then distilled off using a Wiped Film Evaporator by Pope at a temperature of 165° C. and a vacuum of 2 mm Hg. The final sample is a crispy solid with the following analyses: (In the following, e.g., dodecanol polyglycoside with n glucose moieties is abbreviated $C_{12}G_n$). Average glucose number per alkyl chain: 2.0, weight percent of n-butyl oligoglycoside: <5.9%, $C_{12}$, $G_1$: ~40%, $C_{12}$ $G_2$: 21%, $C_{12}$ $G_3$ 13%, $C_{12}$ $G_4$ 98%, $C_{12}$ $G_5$ 8%, >$C_{12}$ $G_6$, <10%, $C_{12}$—OH: 0.46%.

EXAMPLE II 500 ml n-butanol, 48 g anhydrous glucose, 200 ml Neodol 23 and 0.0534 g of p-toluene sulfonic acid were reacted. The reaction was carried out in a 1000 ml flask with vigorous stirring. After n-butanol removal, reaction condition was set at 118° C., 2 cmHg vacuum until 103% of the added n-butanol volume was collected. (Water) After neutralizing in the usual manner, the sample was dried, as in Example I, through the wiped film evaporator. The product was analyzed to be: average glycoside number per alkyl chain: 2.0, weight percent of n-butyl oligoglycoside <1%, $C_{12,13}$ $G_1$ ~49%, $C_{12,13}$ $G_2$: 19%, $C_{12,13}$ $G_3$: 11.5%, $C_{12,13}$ $G_4$: 8.4%, $C_{12,13}$ $G_5$: 4.44%, $C_{12,13}$ $G_6$: 3.85%.

EXAMPLE III 500 ml n-butanol, 192 g anhydrous dextrose, 200 ml Neodol 23 and 0.0534 g p-toluene sulfonic acid. The reaction was carried out in the same manner as Example II. The final product was analyzed to be: average glucose number per alkyl chain: <2.5, $C_{12,13}$ $G_1$: 35%, $C_{12,13}$ $G_2$: 20%., $C_{12,13}$ $G_3$: 15%, $C_{12,13}$ $G_4$: 12.6%, $C_{12,13}$ $G_5$: 9.8%, $C_{12,13}$ $G_6$: 7.6%.

COMPARATIVE EXAMPLE IV 480 g anhydrous dextrose, 6.0 g p-toluene sulfonic acid, 960 g Neodol-23 ($C_{12-13}$ fatty alcohol) and 3600 ml n-butanol were refluxed at 117° C. for 1 hour. The n-butanol was distilled off under atmospheric pressure for 45 minutes at 120° C. The pressure was reduced gradually to 50 mm Hg and the temperature was maintained at 130° C. for 1.5 hours. The reaction mixture was neutralized with 3 g sodium carbonate in 20 ml $H_2O$. The excess alcohol was washed away with acetone. The product had the following analyses: 27% butyl polyglycosides, 10.2 glucose units/per molecule. This indicated the temperature was too high and too much catalyst was used. This favored the polysaccharide chain length polymerization without removing the butyl polyglycosides.

EXAMPLE V 96 g anhydrous dextrose, 200 ml Neodol-23 ($C_{12-13}$ fatty alcohol), 0.4 g p-toluene sulfonic acid and 500 ml n-butanol were refluxed for 2 hours. 95% of the n-butanol was then removed by distillation at 115° C.±5° C. under vacuum. The resulting mixture was then passed through a Pope a-inch Wiped Film Evaporator twice, operated at 120° C., and 2 cm Hg pressure. The reaction mixture before the removal of excess fatty alcohol was the following composition: alkyl polyglycoside: 51%, average glucose per molecule: 2.0, butyl polyglycosides: <5%.

EXAMPLE VI 400 g anhydrous dextrose, 800 ml Neodol-91 ($C_{9-11}$ fatty alcohol), 1.6 g p-toluene sulfonic acid and 2000 ml n-butanol were refluxed for 2 hours. 95% of the butanol was then removed under the same conditions as in Example V. The reaction mixture was passed through a Pope Wiped Film Evaporator twice, the resulting mixture contains: alkyl polyglycoside 48%, average glucose per molecule 1.6, butyl polyglycoside <3%.

Wiped Film Evaporator Examples

EXAMPLE VII 960 g anhydrous dextrose, 2000 ml Neodol-23, 5000 ml n-butanol and 1.2 g concentrated sulfonic acid were refluxed at 117° C. for 2 hours. n-butanol was then removed at 117° C., 2 cm Hg pressure. The reaction mixture was neutralized with $Na_2CO_3$ solution. The excess Neodol-23 was then removed by a 2 inch Pope Wiped Film Evaporator operated at 160°-170° C., 2 mm Hg pressure. The solution residence time in the hot zone was approximately 1 minute. The resulting product has a light brown color. Melting point about 130° C. It was cooled to room temperature and was easily ground into a yellowish powder. Analyses showed a content of 0.45% Neodol-23. It dissolved readily in water and gave a yellowish clear solution.

EXAMPLE VIII 100 g anhydrous dextrose, 200 ml Neodol-91, 500 ml n-butanol and 0.1 g concentrated sulfonic acid were refluxed at 117° C. for 2 hours. n-butanol was then removed at 117° C. and 2 cm Hg pressure. After neutralization by $Na_2CO_3$, the reaction mixture was passed through a 2 inch Pope Wiped Film Evaporator. The operating conditions were 155°-165° C. and 2 mm Hg pressure. A product containing 0.2% Neodol-91 was obtained.

EXAMPLE IX

The same reaction as in Example VII was carried out except 400 ml Neodol-23 was used in place of Neodol-91. The reaction mixture was passed twice through the Pope Wiped Film Evaporator at 165°-170° C. and 2 mm Hg pressure. The product contained 0.4% Neodol-23.

What is claimed is:

1. In the process of removing fatty alcohol containing from about 12 to about 18 carbon atoms from a mixture of said alcohol with an alkyl polysaccharide wherein saccharide chain length is greater than one on the average and less than about 20 the improvement of heating the mixture under vacuum in a thin film evaporator wherein the thin film evaporator provides, in operation, a Reynolds number of at least about 20,000 and a film thickness of less than about 10 mm and the temperature is from about 120° C. to about 200° C. and the vacuum is from about 0.1 to about 20 mm of mercury so that no more than about 2% of said fatty alcohol remains.

2. The process of claim 1 wherein the alkyl polysaccharide comprises an alkyl group of from about 12 to about 18 carbon atoms; the polysaccharide chain is derived from a reducing saccharide containing five or six carbon atoms and there are from about 1½ to about 4 saccharide moieties on the average.

3. The process of claim 2 wherein the reducing saccharide is glucose.

4. The process of claim 1 wherein the Reynolds number is at least about 50,000, the temperature is from about 140° C. to about 180° C., and the vacuum is from about 0.1 to about 5 mm of mercury.

5. The process of claim 2, 3, 4, or 1 wherein the fatty alcohol is removed to a level of less than about ½%.

* * * * *

REEXAMINATION CERTIFICATE (2307th)

United States Patent [19]
Mao et al.

[11] B1 4,393,203
[45] Certificate Issued May 31, 1994

[54] PROCESS OF PREPARING ALKYLPOLSACCHARIDES

[75] Inventors: Mark H. K. Mao, Cincinnati; Larry E. Miller, Madeira; John M. Weeman, Cincinnati, all of Ohio

[73] Assignee: Procter & Gamble Company, Cincinnati, Ohio

Reexamination Requests:
No. 90/002,939, Jan. 28, 1993
No. 90/002,718, May 7, 1992

Reexamination Certificate for:
Patent No.: 4,393,203
Issued: Apr. 26, 1982
Appl. No.: 371,693
Filed: Jul. 12, 1983

[51] Int. Cl.$^5$ .................. C07G 3/00; C07H 1/00; C08B 37/00
[52] U.S. Cl. .................. 536/124; 159/49; 159/DIG. 10; 159/6.2; 536/4.1; 536/18.4; 536/120
[58] Field of Search ............... 536/124, 4.1, 120, 18.5, 536/127, 18.4; 159/6.2, 49

[56] References Cited

U.S. PATENT DOCUMENTS

| | | | |
|---|---|---|---|
| 2,049,758 | 8/1936 | Bertsch et al. | 536/4.1 |
| 2,390,507 | 12/1945 | Cantor | 536/4.1 |
| 2,671,780 | 3/1954 | Gaver et al. | 536/111 |
| 2,671,781 | 3/1954 | Gaver et al. | 536/111 |
| 2,959,500 | 11/1960 | Schlapfer et al. | 127/37 |
| 2,974,134 | 3/1961 | Pollitzer | 536/120 |
| 3,092,618 | 6/1963 | Rosen et al. | 536/103 |
| 3,219,656 | 11/1965 | Boettner | 536/18.3 |
| 3,314,936 | 4/1967 | Ames | 536/120 |
| 3,346,558 | 10/1967 | Roth | 536/18.6 |
| 3,450,690 | 6/1969 | Gibbons et al. | 536/18.5 |
| 3,547,828 | 12/1970 | Mansfield et al. | 252/351 |
| 3,598,865 | 8/1971 | Lew | 260/210 R |
| 3,640,998 | 2/1972 | Mansfield et al. | 536/18.3 |
| 3,707,535 | 12/1972 | Lew | 536/18.6 |
| 3,721,633 | 3/1973 | Ranauto | 252/527 |
| 3,737,426 | 6/1973 | Throckmorton et al. | 536/18.3 |
| 3,777,269 | 11/1973 | Lew | 375/67 |
| 3,839,318 | 10/1974 | Mansfield | 536/18.6 |
| 4,011,389 | 3/1977 | Langdon | 536/4.1 |
| 4,154,706 | 5/1979 | Kenkare et al. | 252/547 |
| 4,187,121 | 2/1980 | Herald et al. | 134/26 |
| 4,223,129 | 9/1980 | Roth et al. | 536/4 |
| 4,240,921 | 12/1980 | Kaniecki | 252/156 |
| 4,309,447 | 1/1982 | Tsutsumi et al. | 424/361 |
| 4,349,669 | 9/1982 | Klahr et al. | 536/127 |

FOREIGN PATENT DOCUMENTS

593422 2/1934 Fed. Rep. of Germany.
3001064 7/1981 Fed. Rep. of Germany.

OTHER PUBLICATIONS

Fischer, Chemical Engineering, pp. 186–190, Sep. 13, 1965 Kirk–Othmer Encyclopedia of Chemical Technology, vol. 12, Third Edition pp. 134–135, (1980).
The Journal of the American Chemical Society, vol. 60, (Sep. 1938), pp. 2076–2077, Noller et al.
Nature, vol. 197, (Mar. 16, 1963) Schram et al. Several Data Sheets, Rohm & Haas Co., Material Safety Data Sheet, Coded 6–1843; a page entitled "Manufacturing Specifications", Triton BG–10; A Specialty Chemicals Price List, schedule CS–429,25; a publication entitled The Qualitative and Quantitative Determination of Triton BG–10 in Bottle Washing Formulations, Coded CS-400.
The Journal of The American Oil Chemist's Society, vol. 47, #5, (May, 1980), pp. 162–167, Hughes et al, "Physical and Functional Properties of Some Higher Alkyl Polyglucosides".
Kirk–Othmer, Encyc. of Chem. Tech. 2d Ed., vol. 9, p. 459 (1972).

*Primary Examiner*—Ronald W. Griffin

[57] ABSTRACT

Long chain fatty alcohols can be removed from alkylpolysaccharide products in thin film evaporators to achieve fatty alcohol levels of less than about 2% without excessive discoloration of the alkylpolysaccharide.

REEXAMINATION CERTIFICATE ISSUED UNDER 35 U.S.C. 307

PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2 and 4 are determined to be patentable as amended.

Claims 3 and 5 dependent on an amended claim, are determined to be patentable.

New claims 6-19 are added and determined to be patentable.

1. In the process of removing fatty alcohol containing from about 12 to 18 carbon atoms from a mixture of said alcohol with [an] *a* $C_{12}$ to $C_{18}$ alkyl polysaccharide wherein saccharide chain length is greater than one on the average and less than about 20 *saccharide moieties, and wherein said mixture contains no $C_1$ to $C_5$ short chain alcohols or auxiliary solvents,* the improvement [of] *which comprises* heating the mixture under *a* vacuum *of from about 0.1 to about 20 mm of mercury* in a thin film evaporator [wherein the thin film evaporator] *which* provides, in operation, a Reynolds number of at least about 20,000 [and] a film thickness of less than about 10 mm and [the] *a film* temperature [is] *of* from about [120° C.] *140° C.* to about 200° C. [and the vacuum is from about 0.1 to about 20 mm of mercury so] , *wherein fatty alcohol removable is continued under the aforesaid conditions so as to avoid decomposition of, and any appreciable change in the color of, said alkylpolysaccharide and continued to the extent* that no more than about 2% of said fatty alcohol remains *in said mixture*.

2. The process of claim 1 wherein [the alkyl polysaccharide comprises an alkyl group of from about 12 to about 18 carbon atoms;] the polysaccharide chain is derived from a reducing saccharide containing five or six carbon atoms and there are from about 1½ to about 4 saccharide moieties on the average.

4. The process of claim 1 wherein the Reynolds number is at least about 50,000, the temperature is from [about 140] *155°* C. to about [180] *200°* C., and the vacuum is from about 0.1 to about 5 mm of mercury.

6. *The process of claim 4 wherein the temperature is from about 160° C. to about 180° C.*

7. *The process of claim 1 wherein the resulting alkyl polysaccharide has an average chain length of from about 1½ to about 3 saccharide moieties and the amount of alkyl polysaccharide in which the saccharide chain length is 6 saccharide moieties or greater is less than about 10%.*

8. *The process of claim 7 wherein the alkyl polysaccharide has an average chain length of from about 1.6 to about 2¼ saccharide moieties, and the amount of alkyl polysaccharide in which the saccharide chain length is 6 saccharide moieties or greater is less than about 5%.*

9. *The process of claim 7 wherein the unreacted fatty alcohol content is less than about ½%.*

10. *The process of claim 9 wherein the alkyl polysaccharide comprises an alkyl group containing from about 12 to about 14 carbon atoms.*

11. *In the process of removing fatty alcohol containing from about 12 to about 18 carbon atoms from a mixture of said alcohol with a $C_{12}$ to $C_{18}$ alkyl polysaccharide wherein saccharide chain length is greater than one on the average and less than about 20 saccharide moieties, wherein said mixture has been formed by the catalyzed reaction of fatty alcohol with short chain alkylsaccharide and wherein said mixture contains no $C_1$ to $C_5$ short chain alcohols or auxiliary solvents, the improvement which comprises heating the mixture under a vacuum of from about 0.1 to about 20 mm of mercury in a thin film evaporator which provides, in operation, a Reynolds number of at least about 20,000, a film thickness of less than about 10 mm and a film temperature of from about 140° C. to about 200° C. wherein fatty alcohol removal is continued under the aforesaid conditions so as to avoid decomposition of, and any appreciable change in the color of, said alkylpolysaccharide and continued to the extent that no more than about 2% of said fatty alcohol remains in said mixture.*

12. *The process of claim 11 wherein the polysaccharide chain is derived from a reducing saccharide containing five or six carbon atoms and there are from about 1½ to about 4 saccharide moieties on the average.*

13. *The process of claim 12 wherein the temperature is from 155° C. to about 200° C.*

14. *The process of claim 12 wherein the reducing saccharide is glucose.*

15. *The process of claim 11 wherein the resulting alkyl polysaccharide has an average chain length of from about 1½ to about 3 saccharide moieties and the amount of alkyl polysaccharide in which the saccharide chain length is 6 saccharide moieties or greater is less than about 10%.*

16. *The process of claim 11 wherein the Reynolds number is at least about 50,000, the temperature is from 155° C. to about 180° C., and the vacuum is from about 0.1 to about 5 mm of mercury.*

17. *The process of claim 14 wherein the alkyl polysaccharide has an average chain length of from about 1.6 to about 2¼ saccharide moieties, and the amount of alkyl polysaccharide in which the saccharide chain length is 6 saccharide moieties or greater is less than about 5%.*

18. *The process of claim 11 wherein the temperature is from about 160° C. to about 180° C.*

19. *The process of claim 10 wherein the unreacted fatty alcohol content is less than about ½%.*

* * * * *

REEXAMINATION CERTIFICATE (3243rd)

United States Patent [19]
Mao et al.

[11] B2 4,393,203
[45] Certificate Issued Jul. 1, 1997

[54] PROCESS OF PREPARING ALKYLPOLYSACCHARIDES

[75] Inventors: Mark H. K. Mao, Cincinnati; Larry E. Miller, Madeira; John M. Weeman, Cincinnati, all of Ohio

[73] Assignee: The Procter & Gamble Company, Cincinnati, Ohio

Reexamination Request:
No. 90/003,353, Mar. 8, 1994

Reexamination Certificate for:
Patent No.: 4,393,203
Issued: Jul. 12, 1983
Appl. No.: 371,693
Filed: Apr. 26, 1982

Reexamination Certificate B1 4,393,203 issued May 31, 1994

Certificate of Correction issued May 31, 1994.

[51] Int. Cl.$^6$ ............... C07G 3/00; C07H 1/00; C08B 37/00
[52] U.S. Cl. ............... 536/124; 159/49; 159/62; 159/DIG. 10; 536/4.1; 536/18.4; 536/120
[58] Field of Search ............... 536/124, 4.1, 18.4, 536/120, 127; 159/49, DIG. 10, 6.2

[56] References Cited

U.S. PATENT DOCUMENTS

| | | | |
|---|---|---|---|
| 2,049,758 | 8/1936 | Bertsch et al. | 536/4.1 |
| 2,390,507 | 12/1945 | Cantor | 536/4.1 |
| 2,671,780 | 3/1954 | Gaver et al. | 536/111 |
| 2,671,781 | 3/1954 | Gaver et al. | 536/111 |
| 2,959,500 | 11/1960 | Schlapfer et al. | 127/37 |
| 2,974,134 | 3/1961 | Pollitzer | 536/120 |
| 3,092,618 | 6/1963 | Rosen et al. | 536/103 |
| 3,219,656 | 11/1965 | Boettner | 536/18.3 |
| 3,314,936 | 4/1967 | Ames | 536/120 |
| 3,346,558 | 10/1967 | Roth | 536/18.6 |
| 3,450,690 | 6/1969 | Gibbons et al. | 536/18.5 |
| 3,547,828 | 12/1970 | Mansfield et al. | 252/351 |
| 3,598,865 | 8/1971 | Lew | 260/210 R |
| 3,640,998 | 2/1972 | Mansfield et al. | 536/18.3 |
| 3,707,535 | 12/1972 | Lew | 536/18.6 |
| 3,721,633 | 3/1973 | Ranauto | 252/527 |
| 3,737,426 | 6/1973 | Throckmorton et al. | 536/18.3 |
| 3,777,269 | 12/1973 | Lew | 375/67 |
| 3,839,318 | 10/1974 | Mansfield | 536/18.6 |
| 4,011,389 | 3/1977 | Langdon | 536/4.1 |
| 4,154,706 | 5/1979 | Kenkare et al. | 252/547 |
| 4,187,121 | 2/1980 | Herald et al. | 134/26 |
| 4,223,129 | 9/1980 | Roth et al. | 536/4 |
| 4,240,921 | 12/1980 | Kaniecki | 252/156 |
| 4,309,447 | 1/1982 | Tsutsumi et al. | 424/361 |
| 4,349,669 | 9/1982 | Klahr et al. | 536/127 |

FOREIGN PATENT DOCUMENTS

| | | | |
|---|---|---|---|
| B1-0092876 | 10/1986 | European Pat. Off. | C07H 15/04 |
| 593422 | 2/1934 | Germany . | |
| 3001064 | 7/1981 | Germany . | |

OTHER PUBLICATIONS

Fischer, Chemical Engineering, pp. 186–190, Sep. 13, 1965.
Kirk–Othmer Encyclopedia of Chemical Technology, vol. 12, Third Edition pp. 134–135, (1980).
Kirk–Othmer, *Encyclopedia of Chemical Technology, Third Edition*, vol. 9, 1980, pp. 478–480.
Fabry et al, "Alkyl Polyglycosides: An Overview of the Parent Situation," *Happi*, Aug. 1994, vol. 31, No. 8, pp. 111–115.
The Journal of the American Chemical Society, vol. 60, (Sep. 1938), pp. 2076–2077, Noller et al.
Nature, vol. 197 (Mar. 16, 1963) Schram et al.
Several Data Sheets, Rohm & Haas Co., Material Safety Data Sheet, Coded 6–1843; a page entitled "Manufacturing Specifications", Triton BG–10; A Specialty Chemicals Price List, schedule CS–429,25; a publication entitled The Qualitative and Quantitative Determination of Triton BG–10 in Bottle Washing Formulations, Coded CS–400.
The Journal of The American Oil Chemist's Society, vol. 47, #5, (May 1980), pp. 162–167, Hughes et al, "Physical and Functional Properties of Some Higher Alkyl Polyglucosides".

*Primary Examiner*—Chhaya D. Sayala

[57] ABSTRACT

Long chain fatty alcohols can be removed from alkylpolysaccharide products in thin film evaporators to achieve fatty alcohol levels of less than about 2% without excessive discoloration of the alkylpolysaccharide.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–9 and 12–19 is confirmed.

Claims 10 and 11 are determined to be patentable as amended.

10. The process of claim 9 wherein the alkyl polysaccharide comprises an alkyl group containing from about 12 to about 14 carbon atoms *and the fatty alcohols removed from said mixture are primary saturated alcohols selected from the group consisting of dodecyl, tridecyl, tetradecyl and pentadecyl alcohols and mixtures thereof.*

11. In the process of removing *primary saturated* fatty alcohol [containing from about 12 to about 18 carbon atoms] *selected from the group consisting of dodecyl, tridecyl, tetradecyl and pentadecyl alcohols and mixtures thereof* from a mixture of said alcohol with a $C_{12}$ to $C_{18}$ alkyl polysaccharide wherein saccharide chain length is greater than one on the average and less than about 20 saccharide moieties, wherein said mixture has been formed by the catalyzed reaction of fatty alcohol with short chain alkylsaccharide and wherein said mixture contains no $C_1$ to $C_5$ short chain alcohols or auxiliary solvents, the improvement which comprises heating the mixture under a vacuum of from about 0.1 to about 20 mm of mercury in a thin film evaporator which provides, in operation, a Reynolds number of at least about 20,000, a film thickness of less than about 10 mm and a film temperature of from about 140° C. to about 200° C., wherein fatty alcohol removal is continued under the aforesaid conditions so as to avoid decomposition of, and any appreciable change in the color of, said alkylpolysaccharide and continued to the extent that no more than about 2% of said fatty alcohol remains in said mixture.

* * * * *